United States Patent
Ma et al.

(10) Patent No.: US 8,671,237 B2
(45) Date of Patent: Mar. 11, 2014

(54) PATIENT MONITORING PLATFORM INTERFACE

(75) Inventors: Wanran Ma, Boulder, CO (US); Bryan Hansen, Mead, CO (US)

(73) Assignee: Covidien LP, Mansfield, MA (US)

( * ) Notice: Subject to any disclaimer, the term of this patent is extended or adjusted under 35 U.S.C. 154(b) by 239 days.

(21) Appl. No.: 13/149,688

(22) Filed: May 31, 2011

(65) Prior Publication Data

US 2012/0311219 A1    Dec. 6, 2012

(51) Int. Cl.
*G06F 13/20* (2006.01)

(52) U.S. Cl.
USPC ........... 710/313; 710/302; 710/303; 710/304; 600/300; 600/309

(58) Field of Classification Search
USPC ................ 600/300–309; 710/302–304, 313
See application file for complete search history.

(56) References Cited

U.S. PATENT DOCUMENTS

| | | | |
|---|---|---|---|
| 5,375,604 A | 12/1994 | Kelly et al. | |
| 5,491,781 A | 2/1996 | Gasperina | |
| 5,724,025 A | 3/1998 | Tavori | |
| 5,830,150 A | 11/1998 | Palmer et al. | |
| 5,871,451 A | 2/1999 | Unger et al. | |
| 5,912,656 A | 6/1999 | Tham et al. | |
| 5,957,838 A | 9/1999 | Rantala | |
| 6,093,146 A | 7/2000 | Filangeri | |
| 6,152,754 A | 11/2000 | Gerhardt et al. | |
| 6,221,012 B1 | 4/2001 | Maschke et al. | |
| 6,325,540 B1 | 12/2001 | Lounsberry et al. | |
| 6,352,504 B1 | 3/2002 | Ise et al. | |
| 6,402,691 B1 | 6/2002 | Peddicord et al. | |
| 6,544,173 B2 | 4/2003 | West et al. | |
| 6,544,174 B2 | 4/2003 | West et al. | |
| 6,579,231 B1 | 6/2003 | Phipps | |
| 6,584,336 B1 | 6/2003 | Ali et al. | |
| 6,658,276 B2 | 12/2003 | Kianl et al. | |
| 6,684,090 B2 | 1/2004 | Ali et al. | |

(Continued)

FOREIGN PATENT DOCUMENTS

| | | |
|---|---|---|
| WO | WO 2005114524 | 12/2005 |
| WO | WO 2006006107 | 1/2006 |
| WO | WO 2006064397 | 6/2006 |
| WO | WO 2010027694 A1 | 3/2010 |

OTHER PUBLICATIONS

Molex—"Part No. 45985-0443—1.27mm Pitch, EXTreme LPHPower Plug with Guides and Pegs"; 2 pages, Dated Oct. 18, 2012.*

(Continued)

*Primary Examiner* — Brian Misiura

(57) ABSTRACT

Physical monitoring systems are disclosed which may include a platform interface between a platform device and a monitoring module. The platform interface may allow physiological information from a patient such as sensor signal data, physiological trend data, other suitable data, or combinations thereof to be communicated from the monitoring module to the platform device. The platform interface may include a connector with pins configured to receive UART communications, transmit UART communications, communicate diagnostic information, be coupled to a ground, be coupled to a serial clock, receive serial data, transmit serial data, be coupled to a regulated power supply, be coupled to an unregulated power supply, communicate using USB standard, communicate using any other suitable standards, perform any other suitable functions, or any combinations thereof. The monitoring module may connect directly to the platform device, or a wired cable with suitable connectors may be used to electrically couple the monitoring module to the platform device.

18 Claims, 3 Drawing Sheets

(56) References Cited

U.S. PATENT DOCUMENTS

| | | | |
|---|---|---|---|
| 6,770,028 B1 | 8/2004 | Ali et al. | |
| 6,792,396 B2 | 9/2004 | Inda et al. | |
| 6,820,050 B2 | 11/2004 | Simmon et al. | |
| 6,850,788 B2 | 2/2005 | Al-Ali | |
| 6,947,780 B2 | 9/2005 | Scharf | |
| 6,996,427 B2 | 2/2006 | Ali et al. | |
| 7,002,468 B2 | 2/2006 | Eveland et al. | |
| 7,249,036 B2 | 7/2007 | Bayne | |
| 7,316,648 B2 | 1/2008 | Kelly et al. | |
| 7,373,193 B2 | 5/2008 | Al-Ali et al. | |
| 7,383,358 B1 | 6/2008 | Kennedy | |
| 7,530,949 B2 | 5/2009 | Ali et al. | |
| 7,542,878 B2 | 6/2009 | Nanikashvili | |
| 7,657,849 B2 | 2/2010 | Chaudhri et al. | |
| 7,702,382 B2 | 4/2010 | Xue et al. | |
| 7,887,345 B2 * | 2/2011 | Wong et al. | 439/140 |
| 8,046,721 B2 | 10/2011 | Chaudhri et al. | |
| 8,131,564 B2 * | 3/2012 | Dicks et al. | 705/2 |
| 8,208,853 B2 * | 6/2012 | Lydon et al. | 455/41.2 |
| 8,238,811 B2 * | 8/2012 | Lydon | 455/3.03 |
| 8,286,103 B2 | 10/2012 | Chaudhri et al. | |
| 8,315,683 B2 * | 11/2012 | Al-Ali et al. | 600/323 |
| 2006/0094936 A1 | 5/2006 | Russ | |
| 2006/0098666 A1 | 5/2006 | Powell et al. | |
| 2006/0229503 A1 | 10/2006 | Fluegel | |
| 2006/0235281 A1 | 10/2006 | Tuccillo | |
| 2007/0004971 A1 | 1/2007 | Riley et al. | |
| 2007/0282177 A1 | 12/2007 | Pilz | |
| 2008/0045809 A1 | 2/2008 | Hermannsson | |
| 2008/0081954 A1 | 4/2008 | Meyer et al. | |
| 2008/0097550 A1 | 4/2008 | Dicks et al. | |
| 2008/0097917 A1 | 4/2008 | Dicks et al. | |
| 2008/0103554 A1 | 5/2008 | Dicks et al. | |
| 2008/0114221 A1 | 5/2008 | Tso | |
| 2008/0191866 A1 | 8/2008 | Falck et al. | |
| 2008/0221404 A1 | 9/2008 | Tso | |
| 2008/0294462 A1 | 11/2008 | Nuhaan et al. | |
| 2009/0325408 A1 | 12/2009 | Wong et al. | |
| 2011/0077473 A1 * | 3/2011 | Lisogurski | 600/301 |
| 2011/0077487 A1 * | 3/2011 | Buxton et al. | 600/324 |
| 2011/0077488 A1 * | 3/2011 | Buxton et al. | 600/324 |
| 2011/0078596 A1 * | 3/2011 | Rawlins et al. | 715/764 |
| 2011/0125601 A1 | 5/2011 | Carpenter et al. | |
| 2012/0029304 A1 * | 2/2012 | Medina et al. | 600/300 |
| 2012/0190944 A1 * | 7/2012 | Thaveeprungsriporn et al. | 600/310 |
| 2012/0311219 A1 * | 12/2012 | Ma et al. | 710/313 |

OTHER PUBLICATIONS

"Apple iPod, iPad and iPhone dock Connector Pinout—AllPinouts"; 3 pages, Dated Sep. 27, 2010.*

International Search Report for Application No. PCT/US2012/040084, 4 pages, mailed on Aug. 2, 2012.

* cited by examiner

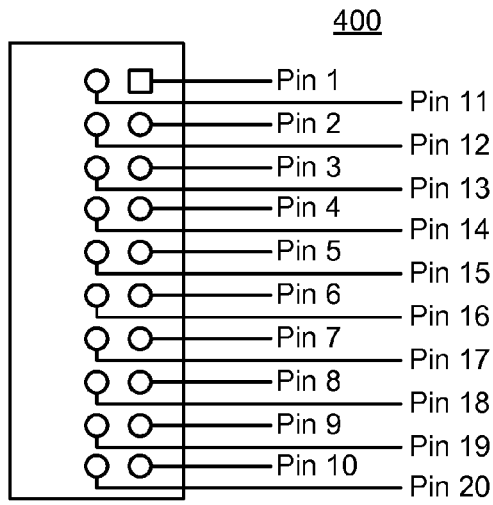

FIG. 4

| Pin | Name | Description |
|---|---|---|
| 1 | Regulated Power | +5 VDC |
| 2 | SCL | I2C Serial Clock |
| 3 | Reserved | Reserved |
| 4 | Nell_TX | UART1 Transmit |
| 5 | UART2_TX | UART2 Transmit |
| 6 | Module_Pret | Digital output; active low when module is connected |
| 7 | Unregulated Power | 12-24 VDC |
| 8 | GND | Ground |
| 9 | USB_N | USB Negative |
| 10 | GND | Ground |
| 11 | Regulated Power | +5 VDC |
| 12 | SDA | I2C Serial Data |
| 13 | Reserved | Reserved |
| 14 | Nell_RX | UART1 Receive |
| 15 | UART2_RX | UART2 Receive |
| 16 | PWRGD | Digital output; active high when module power is OK |
| 17 | Unregulated Power | 12-24 VDC |
| 18 | GND | Ground |
| 19 | USB_P | USB Positive |
| 20 | GND | Ground |

FIG. 5 ical monitoring system. For example, platform device 102 may include a display device as well as any other suitable input/output mechanisms for receiving input from a clinician or other user of physiological monitoring system 100 and for providing output to a clinician or other user of physiological monitoring system 100. Platform device 102 may include any suitable processing circuitry for determining physiological information from information provided by monitoring module 110.

PATIENT MONITORING PLATFORM INTERFACE

The present disclosure relates to a medical device interface, and more particularly, the present disclosure relates to an interface between a medical monitoring platform and a monitoring module.

SUMMARY

A patient monitoring platform interface is provided to communicatively couple a patient monitoring platform device to a monitoring module. The monitoring module may communicate physiological information (e.g., physiological parameter values, sensor signal data) to the platform device. In some embodiments, the patient monitoring platform interface includes a plurality of pins (e.g., an array of 20 pins) configured to electrically and communicatively couple the patient monitoring platform and the monitoring module. The plurality of pins may include at least two pins configured for receiving universal asynchronous receiver/transmitter (UART) communication, at least two pins configured for transmitting UART communication, at least one pin configured for communicating diagnostic information (e.g., whether devices are coupled, whether sufficient power has been provided), at least one pin configured to couple to a ground (e.g., a ground for regulated power, unregulated power, digital data reference), at least one pin configured as a clock, at least one pin configured to receive and transmit serial communications, at least one pin configured as a regulated power supply, and at least two pins configured to a suitable universal serial bus specification.

BRIEF DESCRIPTION OF THE FIGURES

The above and other features of the present disclosure, its nature and various advantages will be more apparent upon consideration of the following detailed description, taken in conjunction with the accompanying drawings in which:

FIG. 4 shows an illustrative platform interface, in accordance with some embodiments of the present disclosure; and FIG. 5 shows an illustrative table of detailed pin descriptions of the illustrative platform interface of FIG. 4, in accordance with some embodiments of the present disclosure.

DETAILED DESCRIPTION OF THE FIGURES

Figure 1:
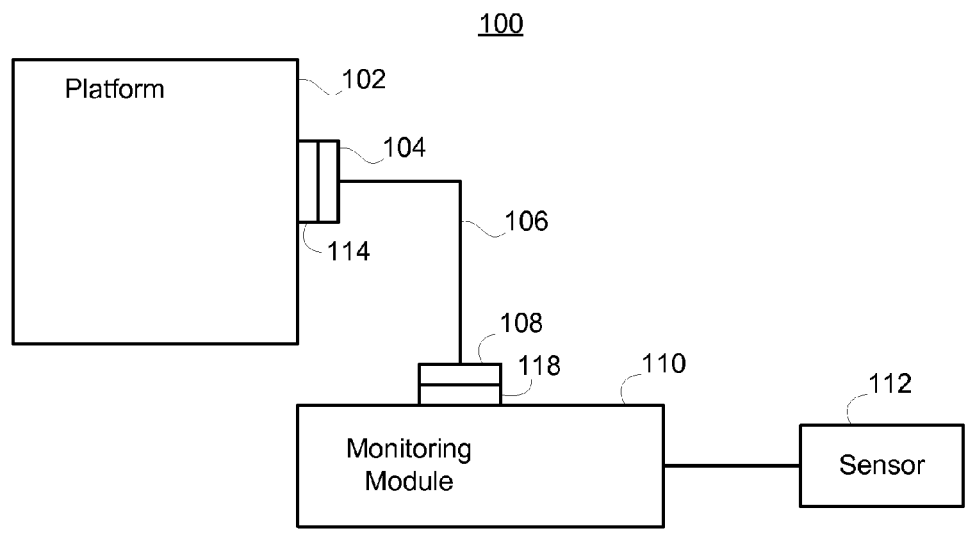
FIG. 1 shows an illustrative patient monitoring system including a platform device coupled to monitoring module using a wired connection, in accordance with some embodiments of the present disclosure.

The present disclosure is directed towards a connection interface between a platform device and a module device that are configured to be communicatively coupled to one another. In some embodiments, the platform device and module device may be part of a physiological monitoring system. For example, FIG. 1 shows an illustrative physiological monitoring system 100 in which platform device 102 is coupled to monitoring module 110 using a wired connection 106, connectors 114 and 118, and connectors 104 and 108 in accordance with some embodiments of the present disclosure. Wired connection 106 may include any suitable cable capable of carrying electrical signals between monitoring module 110 and platform device 102. Wired connection 106 may include any suitable connectors for interfacing with platform device 102 and monitoring module 110, respectively. For example, connectors 104 and 108 may be permanently affixed to wired connection 106 and may each physically engage and communicatively interface with connector 114 on platform device 102 and connector 118 on monitoring module 110.

Platform device 102 may include any suitable hardware, software, or both for implementing a device that may be used as a platform for a physiolog In some embodiments, platform device 102 may be a standalone physiological monitor such as a pulse oximeter and may be used without monitoring module 110. In this case, platform device 102 may be directly coupled to sensors for receiving suitable physiological signals.

Monitoring module 110 may be any suitable software, hardware, or both for calculating or otherwise determining physiological information from physiological signals received from, for example, one or more sensors 112. Physiological information may include sensor signal data, physiological parameter data (e.g., values, trends), any other suitable information, or any combination thereof. In some embodiments, monitoring module 110 may condition or otherwise process (e.g., filter, sample, average, amplify, modulate, transform) a signal received from one or more sensors and communicate the conditioned signal to platform device 102. Sensors 112 may include photoplethysmograph (PPG) sensors, respiratory sensors, electrocardiograph (EKG) sensors, electroencephalograph (EEG) sensors, electromyograph (EMG) sensors, temperature sensors, blood pressure sensors, any other suitable type of physiological sensor, or any combination thereof. Monitoring module 110 may communicate sensor signals, calculated physiological parameter values, calculated physiological parameter trend values, alarm data, message data, status data, device identification data, any other suitable information, or any combination thereof to platform device 102. For example, monitoring module 110 may provide one or more physiological parameters to platform 102 by communicating information indicative of the physiological parameters using wired connection 106 and any suitable ports that interface wired connection 106 between platform device 102 and monitoring module 110.

Monitoring module 110 may be configured to calculate one or more physiological parameters of a patient such as blood oxygen saturation, pulse rate, respiration rate or any other suitable respiratory activity, blood pressure (e.g., systolic, diastolic, or both), blood glucose concentration, any other suitable physiological parameter, or any combination thereof. Monitoring module 110 may be configured to calculate physiological parameter trend data such as, for example, statistical parameters (e.g., an average, a moving average, standard deviation, least squares curve-fit parameters), a change (e.g., a deviation, a relative difference), a rate of change (e.g., a slope, a derivative), any other suitable calculated values, or any combination thereof.

In some embodiments, monitoring module 110 may be a standalone physiological monitoring device such as a pulse oximeter. In some embodiments, in order for monitoring module 110 to be functional, it must be coupled to platform device 102. For example, platform device 102 may be configured to power monitoring module 110 using particular terminals of connectors 104 and 108, and particular wires of wired connection 106. In such an arrangement, monitoring module 110 may not be able to obtain power to function unless coupled to platform device 102 (although, if desired, monitoring module 110 may also be able to obtain power from other external power sources). Monitoring module 110 need not have any display interface or otherwise provide an indication of any information to a clinician or user of physiological monitoring system 100. If desired, however, any suitable indicators or information display may be provided on monitoring module 110. In some embodiments, monitoring module 110 may provide functionality that platform device 102 does not provide, any may be thus used to upgrade the functionality of platform device 102.

The arrangement of platform device 102 and monitoring module 110 may be such that they are apart from one another and wired connection 106 may extend from the location of monitoring module 110 to the location of platform device 102. Alternatively, platform device 102 and monitoring module 110 may be arranged such that they are closely spaced relative to one another and may be physically attached to one another. For example, monitoring module 110 may latch onto platform device 102 using any suitable latching mechanism.

Figure 2:
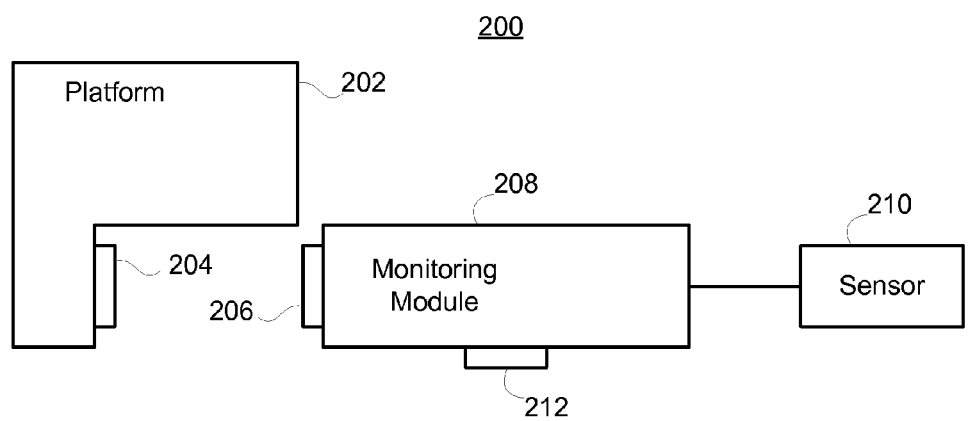
FIG. 2 shows an illustrative patient monitoring system including a monitoring module coupled to a platform device using a direct connection, in accordance with some embodiments of the present disclosure.

FIG. 2 shows an illustrative physiological monitoring system 200 in which monitoring module 208 is coupled to platform device 202 using a direct connection in accordance with some embodiments of the present disclosure. The descriptions of platform device 102 and monitoring module 110 with respect to FIG. 1 generally apply to platform device 202 and monitoring module 208. One of the differences between system 100 and 200 is that wired connection 106 is not used in system 200. Rather, connector 206, which is an input/output port of monitoring module 208, may be coupled directly to connector 204, which is an input/output port of platform device 202. Monitoring module 208 may determine physiological information from physiological signals received from, for example, one or more sensors 210. Sensors 210 may couple to monitoring module 208 using a direct connection, wired connection, wireless coupling, any other suitable coupling, or any combination thereof.

In some embodiments, monitoring module 208 may include connector 212 which is used to connect monitoring module 208 to another monitoring module (not shown but with the same or different functionality compared to monitoring module 208) or other suitable external device, or any combination thereof.

Figure 3:
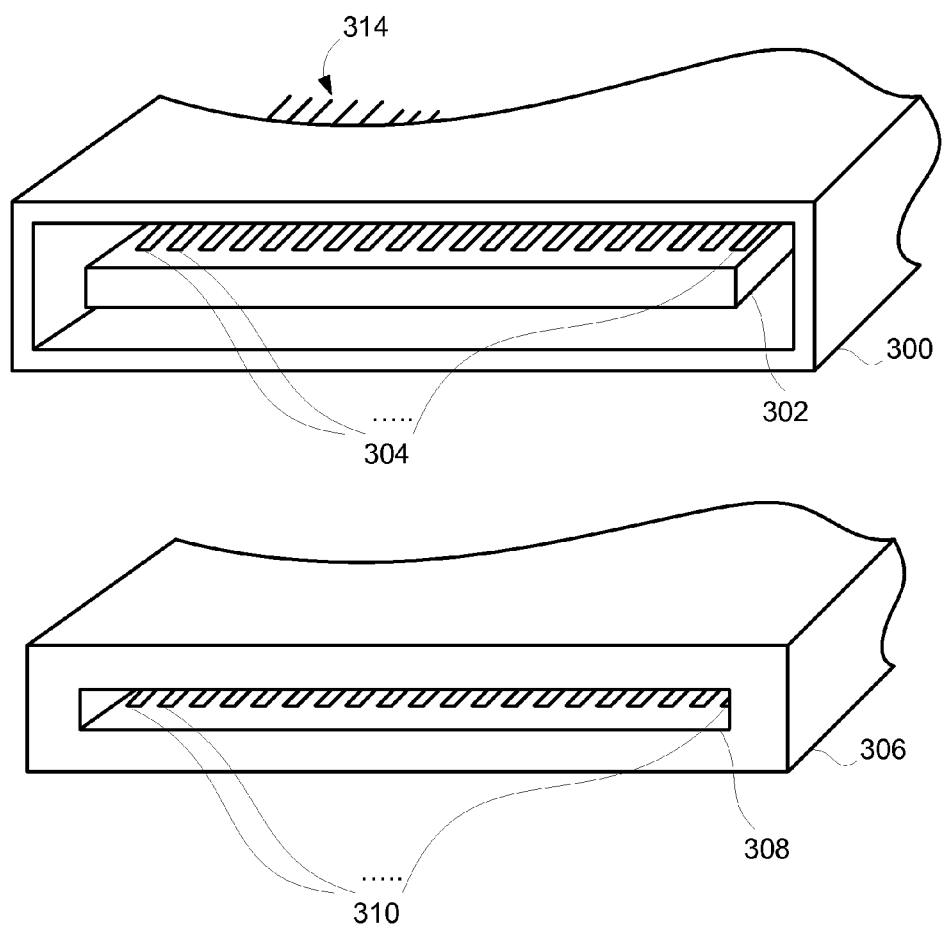
FIG. 3 shows an illustrative first connector configured to communicatively couple to an illustrative second connector, in accordance with some embodiments of the present disclosure.

FIG. 3 shows an illustrative connector 300 which is configured to communicatively couple to an illustrative connector 306, in accordance with some embodiments of the present disclosure. In some embodiments, connectors 300 and 306 may be male and female connectors, respectively, and connector 300 may be plugged into connector 306 to achieve electrical continuity among corresponding electrical terminals of the connectors.

In some embodiments, connector 300 includes electrical terminals 304 which are each electrically coupled to corresponding wires 314. Wires 314 may include electrical insulation, which may prevent shorting or electrical contact between different wires. Wires 314 may be bundled, twisted, sheathed or otherwise arranged in a collection (e.g., a ribbon cable, a sheathed 20-conductor cable). In some embodiments, wires 314 may electrically couple to an additional connector (not shown), circuitry of an electronic device (not shown), or any combination thereof. Electrical terminals 304 may be blades, tabs, sockets, pins, any other suitable type electrical terminal which may be included in a connector, or any combination thereof. Electrical terminals (e.g., electrical terminals 304) and wires (e.g., wires 314) may be configured to transmit direct current (DC) power, alternating current (AC) power, analog signals, digital signals, any other suitable electrical activity, or any suitable combination thereof.

In some embodiments, connector 306 includes electrical terminals 310, which may correspond to electrical terminals 304 of connector 300. For example, connectors 300 and 306 may be connected (e.g., connector 300 may be plugged into connector 306), creating contact between electrical terminals 304 and corresponding terminals of electrical terminals 310. Connecting connector 300 to connector 306 may include inserting male connector portion 302 into female connector portion 308 to create the contact between electrical terminals 304 and electrical terminals 310. In some embodiments, electrical terminals 304 may be arranged on male connector portion 302, and electrical terminals 310 may be arranged in female connector portion 308. In some embodiments, electrical terminals 304 may be pins arranged in a suitable array, and may correspond to electrical terminals 310 which may be holes arranged in a corresponding array. Electrical continuity among corresponding terminals may be formed by plugging the male connector into the female connector, allowing communication among devices electrically coupled to the respective connectors. Connector 300, connector 306, or both, may function as input/output ports for suitable devices (e.g., a patient monitoring platform, a monitoring module).

In an illustrative example, connectors 300 and 306 may be a Molex 45985-0433 male connector and a Molex 46133-0203 female receptacle both manufactured by Molex of Lisle, Ill., respectively, in which the male connector is configured to plug into the female connector. One or both connectors may be soldered or otherwise electrically coupled to a printed circuit board or other suitable circuit arrangement.

FIG. 4 shows an illustrative platform interface 400, in accordance with some embodiments of the present disclosure. FIG. 5 shows an illustrative table 500 of detailed pin descriptions of illustrative platform interface 400. In some embodiments, pin arrangement 400 may include an array of 20 pins, with pin assignments as shown in table 500 of FIG. 5. As shown in table 500, platform interface 400 may include one or more pins configured to provide regulated power (e.g., +5 VDC), unregulated power (e.g., 12-24 VDC), universal serial bus (USB) communication (e.g., using USB 1.1, 2.0, 3.0 or any other suitable USB specification), diagnostics (e.g., for diagnosing when a module is connected to a platform device, or when a module is sufficiently powered), universal asynchronous receiver/transmitter (UART) communication, clock (e.g., inter-integrated circuit (I2C) serial clock), serial data (e.g., I2C serial data), grounding, reserved capacity for future use (e.g., presently unused pins), any other suitable functionality, or any combination thereof. For example, platform interface 400 may include one or more pins for communicating with a Nell-1 OEM board.

In an illustrative example, illustrative platform interface 400 may include 20 pins as shown in FIGS. 4-5.

Platform interface 400 may include one or more pins for supplying regulated DC power to a monitoring module, as shown by pins 1 and 11 of FIGS. 4-5. Regulated power may be supplied by a potential difference between pins 1 and 11, a potential difference between either or both of pins 1 and 11 and one or more ground pins (e.g., pins 8, 10, 18, 20), any other suitable set of pins, or any combination thereof. Platform interface 400 may include one or more pins for supplying unregulated DC power to a monitoring module, as shown by pins 7 and 17 of FIGS. 4-5. Unregulated power may be supplied by a potential difference between pins 7 and 17, a potential difference between either or both of pins 7 and 17 and one or more ground pins (e.g., pins 8, 10, 18, 20), any other suitable set of pins, or any combination thereof. In some embodiments, regulated power of 5 VDC, referenced to a suitable ground, may be provided for digital communications. In some embodiments, an unregulated power supply may be provided for applications requiring more power than a regulated power supply is capable of providing or applications requiring a voltage other than 5 VDC.

Platform interface 400 may include one or more pins for transmitting power, data, or both, using a suitable USB specification (e.g., USB 1.1, 2.0, 3.0). In some embodiments, two pins may be used for digital data transfer, as shown by pins 9 and 19 of FIGS. 4-5. In some embodiments, two pins may be used to supply bus voltage, as shown by pins 1 and 11 of FIGS. 4-5, and two pins may be used to supply ground reference to the supply bus voltage, as shown by pins 10 and 20 of FIGS. 4-5. In some embodiments, four pins such as, for example, pins 1, 9, 19, and 20 may provide the electronic functionality of a Standard type A USB plug connector. In some embodiments, physiological information may be communicated from the monitoring module to a platform using USB data transfer pins.

Platform interface 400 may include one or more pins for communicating diagnostic information, as shown by pins 6 and 16 of FIGS. 4-5. Diagnostic information may include information about when a platform device has been electrically coupled to a monitoring module, whether sufficient power has been supplied to a monitoring module, whether a particular monitoring module is compatible with a platform device, any other suitable diagnostic information, or any combination thereof. In some embodiments, pin 6 of FIGS. 4-5 may be used to communicate information about whether a monitoring module is communicatively coupled to a platform device (e.g., providing an active low if communicatively coupled). In some embodiments, pin 16 of FIGS. 4-5 may be used to communicate information about whether sufficient power has been provided for a monitoring module (e.g., providing an active high when the power is sufficient). Diagnostic information may include message data (e.g., periodic updates), alarm data (e.g., insufficient power, malfunction), warning data (e.g., poor power quality), status data (e.g., monitoring module completely connected to platform, periodic systems check results), any other suitable data, or any combination thereof.

Platform interface 400 may include one or more grounding pins, as shown by pins 8, 10, 18, and 20 of FIGS. 4-5. Grounding pins may be used a reference for a regulated power supply, an unregulated power supply, digital data communication, analog data communication, a digital clock, any other suitable electronic activity, or any combination thereof.

Platform interface 400 may include one or more pins configured for communicating using the I2C interface, as shown by pins 2 and 12 of FIGS. 4-5. The I2C interface may include a serial data line (SDA) as shown by pin 12 and a serial clock (SCL) as shown by pin 2, which may each use a regulated power supply (e.g., 5 VDC as shown by pins 1 and 11), along with a suitable ground as shown by pins 10 and 20. The SDA line may allow digital communications to be received, transmitted, or both.

Platform interface 400 may include one or more pins configured to receive UART communications, as shown by pins 14 and 15 of FIGS. 4-5. Platform interface 400 may include one or more pins configured to transmit UART communications, as shown by pins 4 and 5 of FIGS. 4-5. Any suitable UART may be used in accordance with the present disclosure such as, for example, models 8250, 16450, 16550, and 16950 manufactured by National Semiconductor of Santa Clara, Calif. A UART may include a clock generator, a shift register (e.g., for sending or receiving data), transmit/receive control, read-write control logic, first-in first-out (FIFO) buffer memory for queue processing, any other suitable components, or any combination thereof. In some embodiments, a UART may be a standalone integrated circuit. In some embodiments, a UART may be included in a microcontroller (e.g., a Nell-1 OEM board), integrated circuit, chip, or other suitable electronic assembly. In some embodiments, a UART may be configured to communicate synchronously so that timing (e.g., start, stop) bits are not used in the data stream. In some embodiments, physiological information may be communicated from the monitoring module to a platform using pins configured for UART communications. In some embodiments, platform interface 400 may be configured to receive, transmit, or both, communications for more than one UART, as shown by the designations UART1 (first UART) and UART2 (second UART) of pins 4, 5, 14, and 15 in FIG. 5.

Platform interface 400 may include one or more pins which are not configured, capable of being configured as desired, reserved for future use, or otherwise not functionally assigned, as shown by pins 3 and 13 of FIGS. 4-5. In some embodiments, pins 3 and 13 may be used to provide additional power (regulated or unregulated), provide additional digital communications capacity, provide analog communications capacity, provide additional diagnostics, provide device identification information, any other suitable configuration relative to that shown in FIGS. 4-5, or any combination thereof. In some embodiments, pins 3 and 13 need not be electrically coupled to any circuitry of a monitoring module or platform device.

Although illustratively shown as having 20 pins, platform interface 400 may include any suitable number of pins, arranged in any suitable array which may be, but need not be, patterned. Pins may be arranged in any suitable order according to functionality, polarity, signal type, power level, any other suitable designation, or any combination thereof. Although discusses as "pins", the terminals of platform interface may include any suitable geometry such as, for example, tabs, blades, holes, sockets, any other suitable electrical terminal type, or any combination thereof. In some embodiments, a platform interface may include pins configured according to standards such as, for example, IEEE 1394, parallel small computer system interface (SCSI), serial data interface at 1200 Baud (SDI-12), recommended standard 422 (RS-422), any other suitable standards for data communication, or any combination thereof.

What is claimed is:
1. A monitoring module configured to communicate physiological information to a platform device, the monitoring module comprising:
at least one connector comprising an array of 20 pins, wherein the connector is configured to connect to a corresponding connector of the platform device, the array of 20 pins comprising:

at least two pins configured for receiving UART communications;
at least two pins configured for transmitting UART communications;
at least one pin configured for communicating diagnostic information between the monitoring module and the platform device;
at least one pin configured to be coupled to a ground;
at least one pin configured to be coupled to a serial clock;
at least one pin configured for transmitting and receiving serial communications;
at least one pin configured to be coupled to a regulated power supply;
at least one pin configured to be coupled to an unregulated power supply; and
at least two pins configured for standardized universal serial bus communication between the monitoring module and the platform device, wherein:
the corresponding connector comprises a corresponding plurality of pins for interfacing with the array of 20 pins of the monitoring module connector.

2. The monitoring module of claim 1, wherein the monitoring module further comprises an interface configured to communicatively couple to at least one sensor.

3. The monitoring module of claim 1 further comprising processing circuitry configured to:
process physiological information; and
communicate physiological information to the platform device at a time when the connector is coupled to the corresponding connector of the platform device.

4. The monitoring module of claim 3, wherein the physiological information is provided by the monitoring module to the platform device using at least one of the pins of the array of 20 pins.

5. The monitoring module of claim 3, wherein the physiological information is communicated by the monitoring module to the platform device using the at least two pins configured for transmitting UART communications.

6. The monitoring module of claim 3, wherein the physiological information is communicated by the monitoring module to the platform device using the at least two pins configured for standardized universal serial bus communication.

7. The monitoring module of claim 3, wherein the physiological information is selected from the group consisting of sensor signal data, physiological parameter trend data, alarm data, message data, monitoring module identification information, and/or sensor identification, and/or combinations thereof.

8. The monitoring module of claim 1, wherein the connector is further configured to connect to a wired cable, wherein the wired cable includes a first connector and a second connector arranged at opposite ends of the wired cable, and wherein the first connector is configured to connect to the connector of the monitoring module, and wherein the second connector is configured to connect to the corresponding connector of the platform device.

9. The monitoring module of claim 1, wherein the corresponding plurality of pins of the corresponding connector of the platform device are configured to mate with the array of 20 pins of the connector of the monitoring module.

10. A physiological monitoring system comprising:
a monitoring module comprising a module connector comprising an array of 20 pins, wherein the array of 20 pins comprise:
at least two pins configured for receiving UART communications;
at least two pins configured for transmitting UART communications;
at least one pin configured for communicating diagnostic information between the monitoring module and the platform device;
at least one pin configured to be coupled to a ground;
at least one pin configured to be coupled to a serial clock;
at least one pin configured for transmitting and receiving serial communications;
at least one pin configured to be coupled to a regulated power supply;
at least one pin configured to be coupled to an unregulated power supply; and
at least two pins configured for standardized universal serial bus communication between the monitoring module and the platform device; and
a platform device comprising a platform connector, wherein the platform connector is configured to connect to the module connector, and wherein the platform connector comprises a corresponding plurality of pins for interfacing with the array of 20 pins of the monitoring module connector.

11. The physiological monitoring system of claim 10, wherein the monitoring module further comprises an interface configured to communicatively couple to at least one sensor.

12. The physiological monitoring system of claim 10, wherein the monitoring module further comprises processing circuitry configured to:
process physiological information; and
communicate physiological information to the platform device at a time when the module connector is coupled to the platform connector.

13. The physiological monitoring system of claim 12, wherein the physiological information is provided by the monitoring module to the platform device using at least one of the pins of the array of 20 pins.

14. The physiological monitoring system of claim 12, wherein the physiological information is communicated by the monitoring module to the platform device using the at least two pins configured for transmitting UART communications.

15. The physiological monitoring system of claim 12, wherein the physiological information is communicated by the monitoring module to the platform device using the at least two pins configured for standardized universal serial bus communication.

16. The physiological monitoring system of claim 12, wherein the physiological information is selected from the group consisting of sensor signal data, physiological parameter trend data, alarm data, message data, monitoring module identification information, and/or sensor identification, and/or combinations thereof.

17. The physiological monitoring system of claim 10, wherein the module connector is further configured to connect to a wired cable, wherein the wired cable includes a first connector and a second connector arranged at opposite ends of the wired cable, and wherein the first connector is configured to connect to the module connector, and wherein the second connector is configured to connect to the platform connector.

18. The physiological monitoring system of claim 10, wherein the monitoring module is a first monitoring module, and wherein the module connector is a first connector, the first monitoring module further comprising:

a second connector configured to couple to a second monitoring module, the second connector comprising a plurality of pins, the plurality of pins of the second connector comprising:
  at least two pins configured for receiving UART communications;
  at least two pins configured for transmitting UART communications;
  at least one pin configured for communicating diagnostic information between the first monitoring module and the second monitoring module;
  at least one pin configured to be coupled to a ground;
  at least one pin configured to be coupled to a serial clock;
  at least one pin configured for transmitting and receiving serial communications;
  at least one pin configured to be coupled to a regulated power supply;
  at least one pin configured to be coupled to an unregulated power supply; and
  at least two pins configured for standardized universal serial bus communication between the second monitoring module and the first monitoring module.

* * * * *